United States Patent
Jung et al.

(10) Patent No.: US 9,474,909 B2
(45) Date of Patent: Oct. 25, 2016

(54) WIRELESS MAGNETIC TRACKING

(71) Applicant: Purdue Research Foundation, West Lafayette, IN (US)

(72) Inventors: Byunghoo Jung, West Lafayette, IN (US); Babak Ziaie, West Lafayette, IN (US); Wing Fai Loke, San Jose, CA (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 468 days.

(21) Appl. No.: 13/712,532

(22) Filed: Dec. 12, 2012

(65) Prior Publication Data

US 2013/0166002 A1 Jun. 27, 2013

Related U.S. Application Data

(60) Provisional application No. 61/568,338, filed on Dec. 12, 2011, provisional application No. 61/569,341, filed on Dec. 12, 2011.

(51) Int. Cl.
*A61N 5/00* (2006.01)
*A61N 5/10* (2006.01)

(52) U.S. Cl.
CPC .............. *A61N 5/00* (2013.01); *A61N 5/1049* (2013.01); *A61B 2090/3958* (2016.02); *A61N 2005/1051* (2013.01)

(58) Field of Classification Search
CPC .......... A61B 17/1707; A61B 17/1725; A61B 2019/547; A61B 5/0008; A61B 5/0031
USPC ........................................ 600/9–15; 128/899
See application file for complete search history.

(56) References Cited

U.S. PATENT DOCUMENTS

| | | | |
|---|---|---|---|
| 5,425,367 A * | 6/1995 | Shapiro et al. | 600/424 |
| 5,558,091 A * | 9/1996 | Acker et al. | 600/424 |
| 5,812,065 A * | 9/1998 | Schrott et al. | 340/10.34 |
| 6,484,118 B1 | 11/2002 | Govari | |
| 7,158,754 B2 * | 1/2007 | Anderson | 455/41.1 |
| 2006/0267759 A1* | 11/2006 | Levine | 340/539.12 |
| 2007/0238984 A1* | 10/2007 | Maschke et al. | 600/424 |

OTHER PUBLICATIONS

Loke, W, et al., "Magnetic Tracking System for Radiation Therapy," Aug. 2010, IEEE Transactions on Biomedical Circuits and Systems, vol. 4, No. 4, pp. 223-231.

(Continued)

*Primary Examiner* — Samuel Gilbert
(74) *Attorney, Agent, or Firm* — Purdue Research Foundation

(57) ABSTRACT

Illustrative embodiments of systems and methods for wireless magnetic tracking are disclosed. In one illustrative embodiment, a wireless magnetic tracking system may include a plurality of transmitting coils each configured to generate a magnetic field when energized, an active transponder configured to simultaneously (i) obtain measurements of the magnetic field when one of the plurality of transmitting coils is energized and (ii) transmit a wireless signal containing data concerning the measurements, and a computing device configured to (i) cause each of the plurality of transmitting coils to be sequentially energized, (ii) receive the data concerning the measurements, and (iii) determine a position and an orientation of the active transponder relative to the plurality of transmitting coils in response to the data concerning the measurements.

15 Claims, 15 Drawing Sheets

(56) References Cited

OTHER PUBLICATIONS

Paperno, E., et al., "A New Method for Magnetic Position and Orientation Tracking," Jul. 2001, IEEE Transaction on Magnetics, vol. 37, No. 4, pp. 1938-1940.

Paperno, E., et al., "Three-Dimensional Magnetic Tracking of Biaxial Sensors," May 2004, IEEE Transaction on Magnetics, vol. 40, No. 3, pp. 1530-1536.

Plotkin, A., et al., "3-D Magnetic Tracking of a Single Subminiature Coil With a Large 2-D Array of Uniaxial Transmitters," Sep. 2003, IEEE Transaction on Magnetics, vol. 39, No. 5, pp. 3295-3297.

Raab, F., et al., "Magnetic Position and Orientation Tracking System," Sep. 1979, IEEE Transactions on Aerospace and Electronic Systems, vol. AES-15, No. 5, pp. 709-718.

Seiler, P., et al., "A novel tracking technique for the continuous precise measurement of tumour positions in conformal radiotherapy," 2000, Phys. Med. Biol. 45, pp. N103-N110.

\* cited by examiner

WIRELESS MAGNETIC TRACKING

CROSS-REFERENCE TO RELATED APPLICATIONS

This application claims priority under 35 U.S.C. §119(e) to U.S. Provisional Patent Application Ser. Nos. 61/569,338 and 61/569,341, both filed on Dec. 12, 2011, the entire disclosures of which are incorporated herein by reference.

STATEMENT REGARDING FEDERALLY SPONSORED RESEARCH

This invention was made with government support under Grant No. EB007256 awarded by the National Institutes of Health. The government has certain rights in the invention.

BACKGROUND

The present disclosure relates to systems and methods for wireless magnetic tracking, which may be used, by way of example, during radiation therapy. Radiation therapy is an effective therapeutic modality for combating malignant tumors. During external beam radiation therapy, an external source of ionizing radiation is used to irradiate cancerous cells. Intensity-Modulated Radiation Therapy ("IMRT") is one form of external beam radiation therapy in which the ionizing radiation is broken into many pencil-thin beams using a multi-leaf collimator. During IMRT, these pencil-thin beams enter the body from various angles and conform to the shape of a tumor, thereby reducing irradiation of (and, hence, damage to) surrounding healthy tissues. Accurate, real-time knowledge of the position and orientation of the tumor is needed to maximize the dosage of radiation to cancerous cells while minimizing the dosage of radiation to surrounding healthy cells. Respiration, circulation, and/or peristalsis, however, often cause movement of a patient's organs and, thus, the tumor during radiation therapy.

Several magnetic tracking systems have been utilized to estimate the position of a tumor during radiation therapy. Generally, these systems include a transponder that is implanted in or near the tumor and has one or more magnetic sensors for measuring the strength of a magnetic field generated by excitation coils located near the patient. Mapping the strength and direction of the generated magnetic field at the location of the transponder allows the position of the tumor to be tracked. Many existing wireless magnetic tracking systems use passive transponders, which require temporally separated excitation and measurement periods. The inability to gather position data during excitation of the magnetic sensors in passive transponders slows down the tracking speed of such systems. Furthermore, existing wireless magnetic tracking systems typically use a large number of excitation coils, which further slows down their tracking speeds.

SUMMARY

According to one aspect, a wireless magnetic tracking system may include a plurality of transmitting coils each configured to generate a magnetic field when energized, an active transponder configured to simultaneously (i) obtain measurements of the magnetic field when one of the plurality of transmitting coils is energized and (ii) transmit a wireless signal containing data concerning the measurements, and a computing device configured to (i) cause each of the plurality of transmitting coils to be sequentially energized, (ii) receive the data concerning the measurements, and (iii) determine a position and an orientation of the active transponder relative to the plurality of transmitting coils in response to the data concerning the measurements.

In some embodiments, the active transponder may be adapted to be implantable in a patient's tissue. The active transponder may include at least two magneto-resistive sensors, where each of the at least two magneto-resistive sensors is configured to measure a different component of the magnetic field. The active transponder may include three magneto-resistive sensors that are configured to measure components of the magnetic field that are normal to one another.

In some embodiments, the wireless magnetic tracking system may further include a coil driver circuit configured to selectively supply an excitation signal to each of the plurality of transmitting coils. The computing device may be configured to control the coil driver circuit. The computing device may be configured to control the coil driver circuit such that each of the plurality of transmitting coils is energized over an integer multiple of a period of the excitation signal. The computing device may be configured to control the coil driver circuit such that each of the plurality of transmitting coils is grounded when not being energized. The active transponder may include a wireless transmitter with a carrier radio frequency that is greater than a frequency of the excitation signal. The excitation signal may be a pulsed direct-current excitation signal.

In some embodiments, the wireless magnetic tracking system may further include a receiver configured to (i) receive the wireless signal from the active transponder and (ii) provide the data concerning the measurements to the computing device. The receiver may include a plurality of antennas configured to simultaneously receive the wireless signal from the active transponder and a combiner configured to sum the wireless signals received by the plurality of antennas. The receiver may be configured to integrate a multiplication product of the wireless signal received from the active transponder and the excitation signal supplied by the coil driver circuit.

In some embodiments, the wireless magnetic tracking system may further include an additional active transponder. The additional active transponder may be configured to simultaneously (i) obtain additional measurements of the magnetic field when one of the plurality of transmitting coils is energized and (ii) transmit an additional wireless signal containing data concerning the additional measurements. The wireless signal and the additional wireless signal may have different carrier radio frequencies.

In some embodiments, the computing device may be configured to determine the position and the orientation of the active transponder relative to the plurality of transmitting coils in six degrees of freedom. The computing device may be configured to determine the position and the orientation of the active transponder relative to the plurality of transmitting coils using an iterative method with a previously determined position and orientation of the active transponder as an initial guess. The computing device may be configured to re-determine the position and the orientation of the active transponder relative to the plurality of transmitting coils each time another one of the plurality of transmitting coils is energized. The computing device may be configured to determine the position and the orientation of the active transponder relative to the plurality of transmitting coils with an error of less than 5 millimeters.

In any of the foregoing embodiments, the plurality of transmitting coils may consist of only two transmitting coils.

According to another aspect, an active transponder for wireless magnetic tracking may include a plurality of magneto-resistive sensors, each of the plurality of magneto-resistive sensors being configured to measure a different component of a magnetic field, an analog-to-digital converter ("ADC") configured to convert an analog voltage signal output by one of the plurality of magneto-resistive sensors into a digital signal, a transmitter configured to generate an output signal by modulating a carrier signal with the digital signal, and an antenna configured to broadcast the output signal.

In some embodiments, the plurality of magneto-resistive sensors may include three magneto-resistive sensors that are configured to measure components of the magnetic field that are normal to one another. Each of the plurality of magneto-resistive sensors may include an enable switch configured to selectively connect the magneto-resistive sensor to a supply voltage. The active transponder may further include a controller configured to sequentially activate the enable switch of each of the plurality of magneto-resistive sensors.

In some embodiments, the active transponder may further include a sensor front-end circuit configured to amplify the analog voltage signal output by one of the plurality of magneto-resistive sensors before the analog voltage signal is supplied to the ADC. The transmitter, the ADC, the controller, and the sensor front-end circuit may be implemented on an integrated circuit chip and may have a combined chip area of less than four square millimeters. The analog voltage signal supplied to the ADC may be linearly related to the magnetic field when the magnetic field is between 0 gauss and 1.5 gauss. The ADC may be a successive approximation register ADC.

In some embodiments, the transmitter may include an integer-N phase-locked loop ("PLL") configured to generate the carrier signal. The integer-N PLL may include a phase frequency detector, a charge pump, a voltage-controlled oscillator, and a frequency divider. The charge pump may include dynamic threshold transistors, where a body and a gate of each of the dynamic threshold transistors are electrically coupled to one another. The frequency divider may include a pulse-swallow counter with a dual-modulus prescaler.

In some embodiments, the active transponder may further include a dosimeter configured to measure an amount of radiation delivered to the active transponder and supply a measurement signal indicating the amount of radiation to the ADC. The active transponder may further include a power supply configured to wirelessly receive energy at a frequency between 1 MHz and 10 MHz. The transmitter, the ADC, and the plurality of magneto-resistive sensors may each use a supply voltage of about 500 millivolts.

In any of the foregoing embodiments, the active transponder may have a total power consumption that is less than 1 milliwatt.

BRIEF DESCRIPTION OF THE DRAWINGS

The invention described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

DETAILED DESCRIPTION OF THE DRAWINGS

Figure 1:
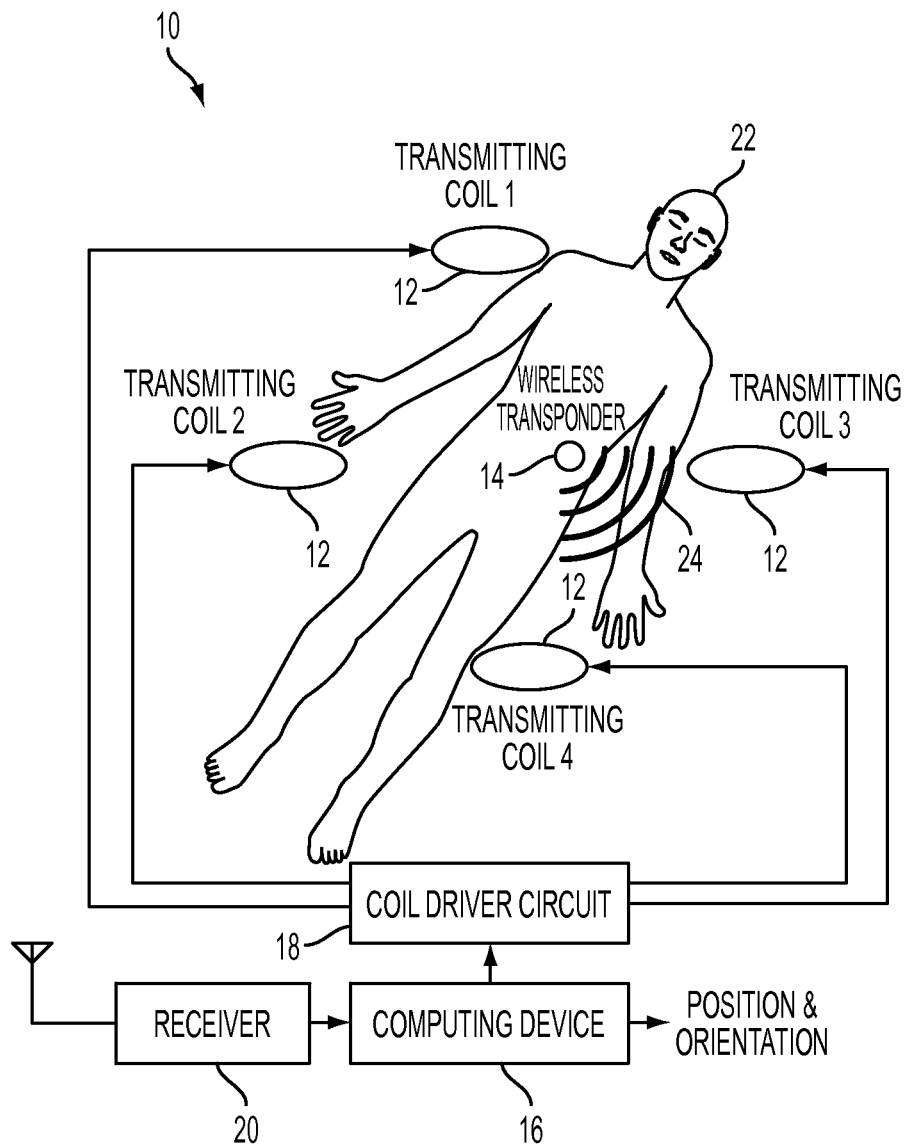
FIG. 1 is a simplified diagram of at least one embodiment of a wireless magnetic tracking system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and appended claims.

In the following description, numerous specific details may be set forth in order to provide a more thorough understanding of the present disclosure. It will be appreciated, however, by one skilled in the art that embodiments of the disclosure may be practiced without such specific details. In other instances, control structures, gate level circuits, and full software instruction sequences have not been shown in detail in order not to obscure the invention. Those of ordinary skill in the art, with the included descriptions, will be able to implement appropriate functionality without undue experimentation.

References in the specification to "one embodiment," "an embodiment," "an illustrative embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention implemented in a wireless magnetic tracking system may include one or more bus-based, or link-based, interconnects between components and/or one or more point-to-point interconnects between components. Embodiments of the invention may also be implemented as instructions carried by or stored on one or more machine-readable media, which may be read and executed by one or more processors. A machine-readable medium may be embodied as any device, mechanism, or physical structure for storing or transmitting information in a form readable by a machine (e.g., a processor). For example, a machine-readable medium may be embodied as read only memory (ROM); random access memory (RAM); magnetic disk storage media; optical storage media; flash memory devices; mini- or micro-SD cards, memory sticks, electrical signals, and others.

In the drawings, specific arrangements or orderings of schematic elements, such as those representing devices, components, modules, instruction blocks, and data elements, may be shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements (e.g., solid or dashed lines or arrows) are used to illustrate a connection, relationship, or association between or among two or more elements, the absence of any such connecting elements is not meant to imply that no connection, relationship or association can exist. In other words, some connections, relationships or associations between elements may not be shown in the drawings so as not to obscure the disclosure. In addition, for ease of illustration, a single connecting element may be used to represent multiple connections, relationships, or associations between elements. For example, where a connecting element represents a communication of signals, data, or instructions, it should be understood by those skilled in the art that such element may represent one or multiple signal paths (e.g., a bus), as may be needed, to effect the communication.

The present disclosure generally relates to systems and methods for wireless magnetic tracking, which may be used, by way of example, during radiation therapy. One illustrative embodiment of a wireless magnetic tracking system 10 is shown as a simplified diagram in FIG. 1. In this illustrative embodiment, the wireless magnetic tracking system 10 includes a plurality of transmitting coils 12, an active wireless transponder 14, a computing device 16, a coil driver circuit 18, and a receiver 20. FIG. 1 illustrates the wireless magnetic tracking system 10 being used to track a tumor during radiation therapy. As such, the transponder 14 has been implanted in a patient 22 at or near the location of a tumor. As described below, the wireless magnetic tracking system 10 is able to track the location of the transponder 14 (and, hence, the tumor) in real-time, allowing radiation therapy to be delivered to the tumor while reducing exposure to healthy surrounding tissues of the patient 22.

In the illustrative embodiment of FIG. 1, the wireless magnetic tracking system 10 includes four transmitting coils 12 that are arranged in a planar array and that are each configured to generate a magnetic field when energized. Although four transmitting coils 12 are included in this embodiment, it is contemplated that the wireless magnetic tracking system 10 may include more or fewer transmitting coils 12 in other embodiments. The transmitting coils 12 may be formed of any material suitable for generating a magnetic field in response to an excitation signal. In the illustrative embodiment, the transmitting coils 12 each include 500 turns and have a diameter of about 21 centimeters. As will be described further below, the coil driver circuit 18, which is under the control of the computing device 16, is configured to selectively supply an excitation signal to each of the transmitting coils 12.

The transponder 14 is an active device, as it is configured to simultaneously obtain measurements of a magnetic field generated by one of the transmitting coils 12 and transmit a wireless signal 24 containing data concerning these measurements. The active transponder 14 may be contrasted with passive devices, which are unable to obtain measurements and transmit data simultaneously. As will be described further below, the transponder 14 generally includes two or three anisotropic magneto-resistive sensors, each of which is configured to measure a different component of a magnetic field generated by one of the transmitting coils 12. These magneto-resistive sensors may be arranged to measure components of the magnetic field that are normal to one another. In other words, illustrative embodiments of the transponder 14 may include a bi-axial or tri-axial magnetic sensor. The transponder 14 also generally includes a wireless transmitter for transmitting data concerning the measurements made by the transponder 14. In some embodiments, this wireless transmitter (described further below) may utilize a carrier radio frequency that is greater than a frequency of the excitation signal produced by the coil driver circuit 18 (and, hence, the magnetic field produced by one of the transmitting coils 12). Although only one transponder 14 is shown in the illustrative embodiment of FIG. 1, it is contemplated that any number of active transponders 14 may be used in other embodiments of the wireless magnetic tracking system 10. In such embodiments, the wireless signals 24 produced by each active transponder 14 may utilize a different carrier frequency (to avoid cross-talk).

The wireless magnetic tracking system 10 also includes a computing device 16 that generally controls operation of many of the components of the system 10. In particular, the computing device 16 may be configured to cause each of the transmitting coils 12 to be sequentially energized, to receive data concerning the measurements performed by the transponder 14, and to determine a position and an orientation of the transponder 14 relative to the transmitting coils 12 in response to the received data. The computing device 16 may be embodied as any type of electronic device capable of performing the functions described herein. By way of illustrative example, the computing device 16 may be embodied as a personal computer, a workstation, a server, a laptop computer, a handheld computer, or any other suitable computer-based device. As shown in FIG. 1, the computing device 16 is communicatively coupled to the coil driver circuit 18 (which is in turn coupled to each of the transmitting coils 12) and to the receiver 20 (which receives the wireless signal 24 from the transponder 14 and provides data to the computing device 16, as described further below).

Figure 2:
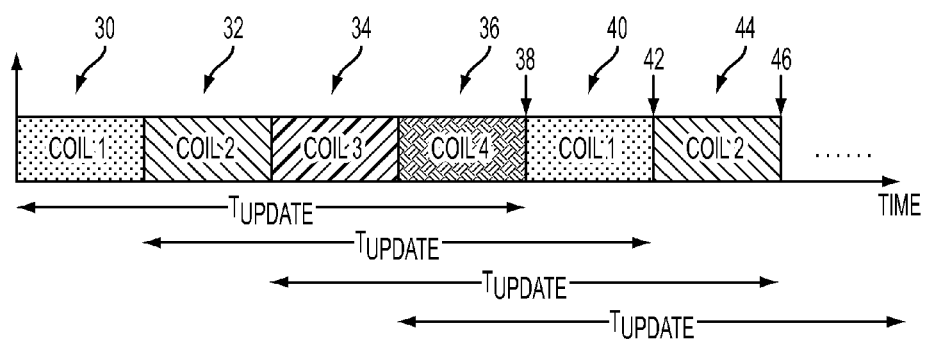
FIG. 2 is a timing diagram for at least one embodiment of a method of operating the wireless magnetic tracking system of FIG. 1.

Referring now to FIG. 2, an illustrative method of operating the wireless magnetic tracking system 10 is illustrated by way of a timing diagram. During a first time period 30, the computing device 16 causes the coil driver circuit 18 to supply an excitation signal to one of the transmitting coils 12 (i.e., "Coil 1"). The excitation signal supplied to the transmitting coil 12 may be any electrical signal that causes the transmitting coil 12 to generate a magnetic field. In some embodiments (illustrated in FIGS. 3 and 4), the excitation signal may be sinusoidal (e.g., an 90 hertz, 1 amp root-mean-square ("RMS") signal). In other embodiments, the excitation signal may be a pulsed, direct-current (DC) excitation signal. In the illustrative embodiment, the remaining transmitting coils 12 (i.e., "Coils 2-4") will not be excited by the coil driver circuit 18 during the first time period 30 and, thus, will not generate any magnetic fields during the first time period 30. Using a number of magnetic sensors, the transponder 14 senses and measures the magnetic field generated by Coil 1 during the first time period 30. Simultaneously (i.e., also during the first time period 30), the transponder 14 transmits a wireless signal 24 containing data concerning these measurements to the receiver 20, which in turn provides the data to the computing device 16.

In the illustrative embodiment, the operations performed with respect to Coil 1 during the first time period 30 are performed with respect to each of Coil 2, Coil 3, and Coil 4 during a second time period 32, a third time period 34, and a fourth time period 36, respectively. Thus, as operation of the wireless magnetic tracking system 10 moves through these time periods 32-36, the computing device 16 causes the transmitting coils 12 to be sequentially energized. During each of the time periods 32-36, the computing device 16 receives data concerning measurements of a number of components of the magnetic field (this number being equal to the number of magneto-resistive sensors present in the transponder 14). Thus, where the transponder 14 includes a bi-axial sensor, each time period 32-36 will provide the computing device 16 with data relating to two magnetic field components (i.e., two equations). Where the transponder 14 includes a tri-axial sensor, each time period 32-36 will provide the computing device 16 with data relating to three magnetic field components (i.e., three equations).

Once the computing device 16 has the information needed to formulate six equations, the computing device 16 can solve the set of six equations for six unknowns: the position of the transponder 14 in three dimensions and the orientation of transponder 14 in three dimensions. At that point, the computing device 16 is able to determine the position and the orientation of the transponder 14 relative to the transmitting coils 12 in six degrees of freedom. This computing device 16 may solve this set of six equations using an iterative method that begins with an initial guess. In some embodiments, this initial guess may be a previously determined position and orientation of the transponder 14. In the illustrative embodiment of FIG. 2, the computing device 16 first calculates the position and orientation of the transponder 14 at time 38, using the data received during time periods 30, 32, 34, 36. During a fifth time period 40, Coil 1 is again energized by the coil driver circuit 18. The computing device 16 may then recalculate the position and orientation of the transponder 14 at time 42, using the data received during time periods 32, 34, 36, 40. Likewise, the computing device 16 may recalculate the position and orientation of the transponder 14 at time 46, using the data received during time periods 34, 36, 40, 44. In other words, the computing device 16 is able to re-determine the position and the orientation of the transponder 14 relative to the transmitting coils 12 each time another one of the transmitting 12 coils is energized.

Figure 3:
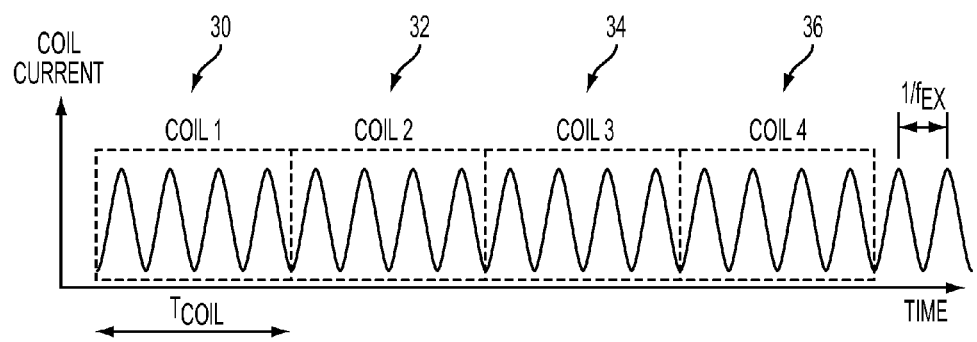
FIG. 3 illustrates at least one embodiment of an excitation signal that may be applied to a plurality of transmitting coils of the wireless magnetic tracking system of FIG. 1.

One illustrative example of a sinusoidal excitation signal that may be supplied to the transmitting coils 12 by the coil driver circuit 18 is shown in FIG. 3. In this illustrative embodiment, the length ($T_{coil}$) of each of the time periods 32-36 is an integer multiple of the period of the excitation signal (the period being equal to the inverse of the frequency of the excitation signal, $1/f_{EX}$). In other words, the period ($1/f_{EX}$) of the excitation signal is multiplied by an integer, N, to arrive at the length ($T_{coil}$) of each of the time periods 32-36. This condition ensures that the phase of the excitation signal during each time period 32-36 will be the same, simplifying the calculations to be performed by the computing device 16 during determination of the position and the orientation of the transponder 14.

Figure 4:
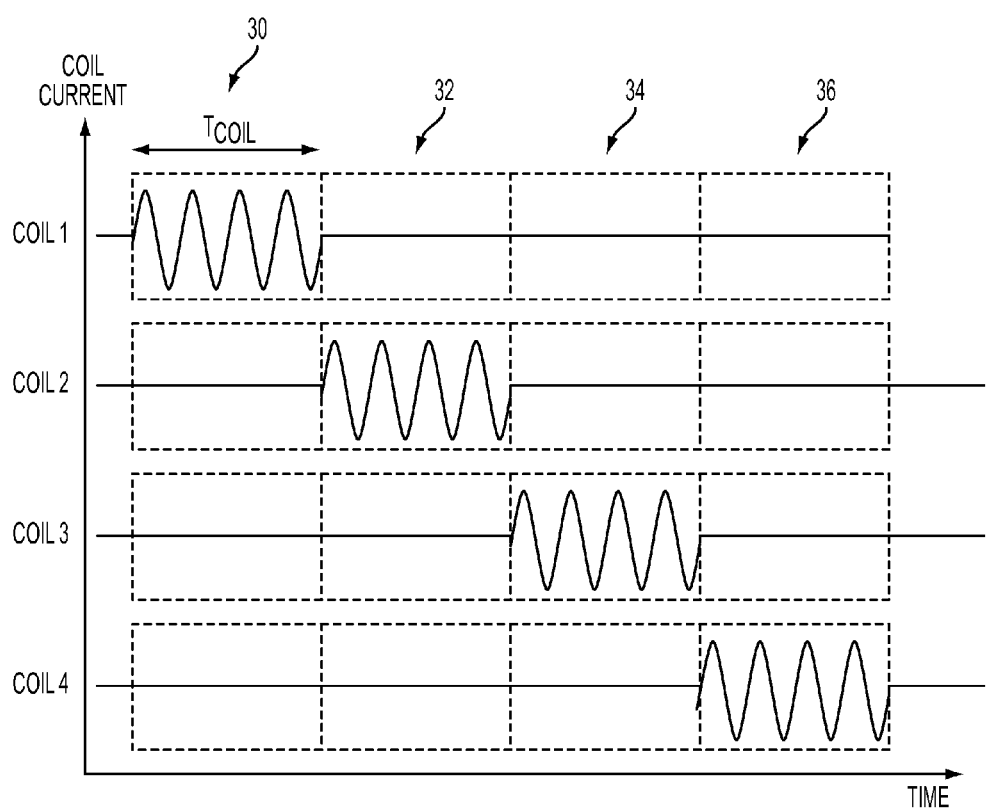
FIG. 4 illustrates the excitation signal being applied sequentially to each of the plurality of transmitting coils of the wireless magnetic tracking system of FIG. 1.

The sequential application of an excitation signal to each of the transmitting coils 12 of the wireless magnetic tracking system 10 is further illustrated in FIG. 4. As shown in FIG. 4, during the first time period 30, the excitation signal is supplied only to Coil 1 by the coil driver circuit 18. Similarly, during the time periods 34, 36, 38, the excitation is supplied only to Coil 2, Coil 3, and Coil 4, respectively. To avoid undesirable ringing (i.e., the continued generation of magnetic fields) by the transmitting coils 12 after their designated excitation times, each of the transmitting coils may be grounded when it is not being energized. For instance, during time periods 34, 36, 38, Coil 1 may be electrically coupled to ground to impede the generation of any magnetic fields. In some embodiments, the coil driver circuit 18 may include one or more switches that selectively couple one or both leads of each transmitting coil 12 to a ground terminal. During the designated excitation period for a transmitting coil 12, these switches may be opened, allowing the transmitting coil 12 to generate a magnetic field in response to an excitation signal; at all other times, these switches may be closed, grounding the transmitting coil 12 and reducing any ringing of the transmitting coil 12.

Figure 5:
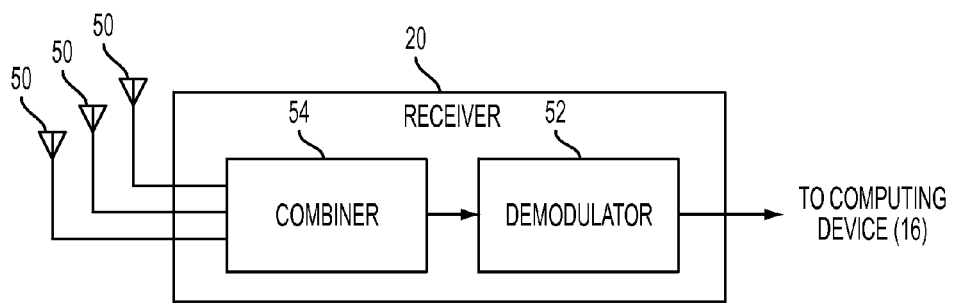
FIG. 5 is a simplified diagram of at least one embodiment of a receiver of the wireless magnetic tracking system of FIG. 1.
Figure 6:
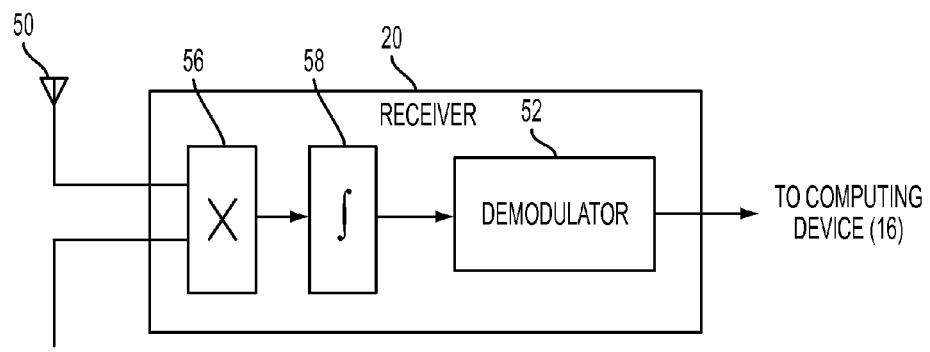
FIG. 6 is a simplified diagram of another embodiment of the receiver of the wireless magnetic tracking system of FIG. 1.
Figure 7:
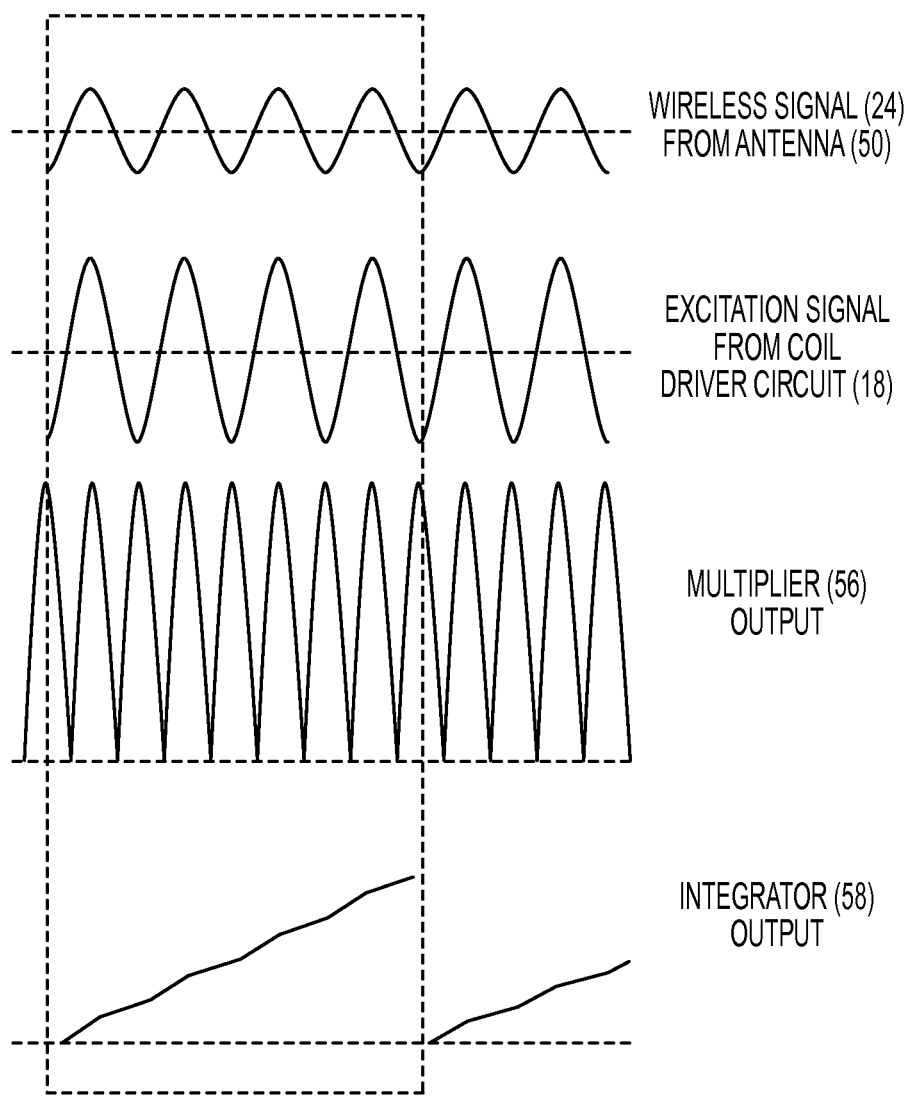
FIG. 7 illustrates various signals present during operation of the receiver of FIG. 6.

Referring now to FIGS. 5-7, illustrative embodiments of the receiver 20 that improve the signal-to-noise ratio ("SNR") of the wireless magnetic tracking system 10 are disclosed. As noted above, the receiver 20 receives the wireless signal 24 from the transponder 14 via an antenna 50, demodulates the wireless signal 24 using a demodulator 52, and provides data concerning the measurements obtained by the transponder 14 to the computing device 16. In the illustrative embodiment of FIG. 5, the receiver 20 includes multiple antennas 50 that simultaneously receive the wireless signal 24. The receiver 20 of FIG. 5 also includes a combiner 54 that sums the copies of the wireless signal 24 received by the multiple antennas 50 prior to providing the wireless signal 24 to the demodulator 52. As these copies of the wireless signal 24 will add constructively in the combiner 54, while random noise will not, the SNR of the system 10 is improved in this embodiment.

In the illustrative embodiment of FIG. 6, the receiver 20 utilizes correlation-based optimal detection to improve the SNR of the system 10. The receiver 20 of this embodiment includes a multiplier 56 followed by an integrator 58. The inputs to the multiplier 56 are the wireless signal 24 received by the antenna 50 from the transponder 14 and the excitation signal supplied by the coil driver circuit 18 (the output of the multiplier 56 being a multiplication product of these two signals). As illustrated in FIG. 7, data contained in the wireless signal 24 will multiply constructively with the excitation signal, while random noise will not. The output of the multiplier 56 may then be added using integrator 58, thus, improving the SNR of the system 10.

Figure 8:
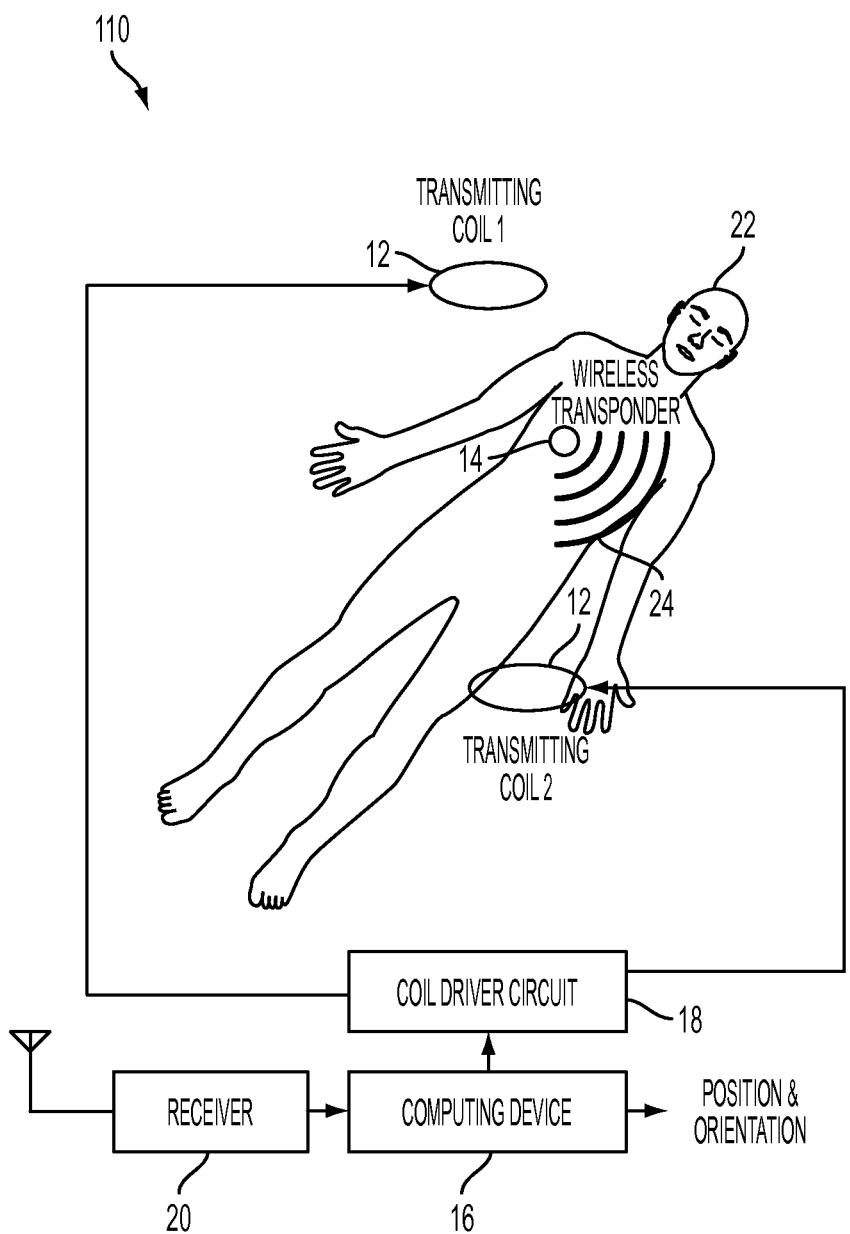
FIG. 8 is a simplified diagram of another embodiment of a wireless magnetic tracking system.

Referring now to FIG. 8, another illustrative embodiment of a wireless magnetic tracking system 80 is shown as a simplified diagram. The wireless magnetic tracking system 80 may include similar components to those described above with respect to the wireless magnetic tracking system 10, except that the wireless magnetic tracking system 80 includes only two transmitting coils 12. The wireless magnetic tracking system 80 may operate using similar methods to those described above with regard to the wireless magnetic tracking system 10, adjusted for two transmitting coils 12. When the wireless magnetic tracking system 80 is used with a transponder 14 including a tri-axial magnetic sensor, the computing device 16 may determine the position and the orientation of the transponder 14 relative to the transmitting coils 12 in six degrees of freedom.

Figure 9:
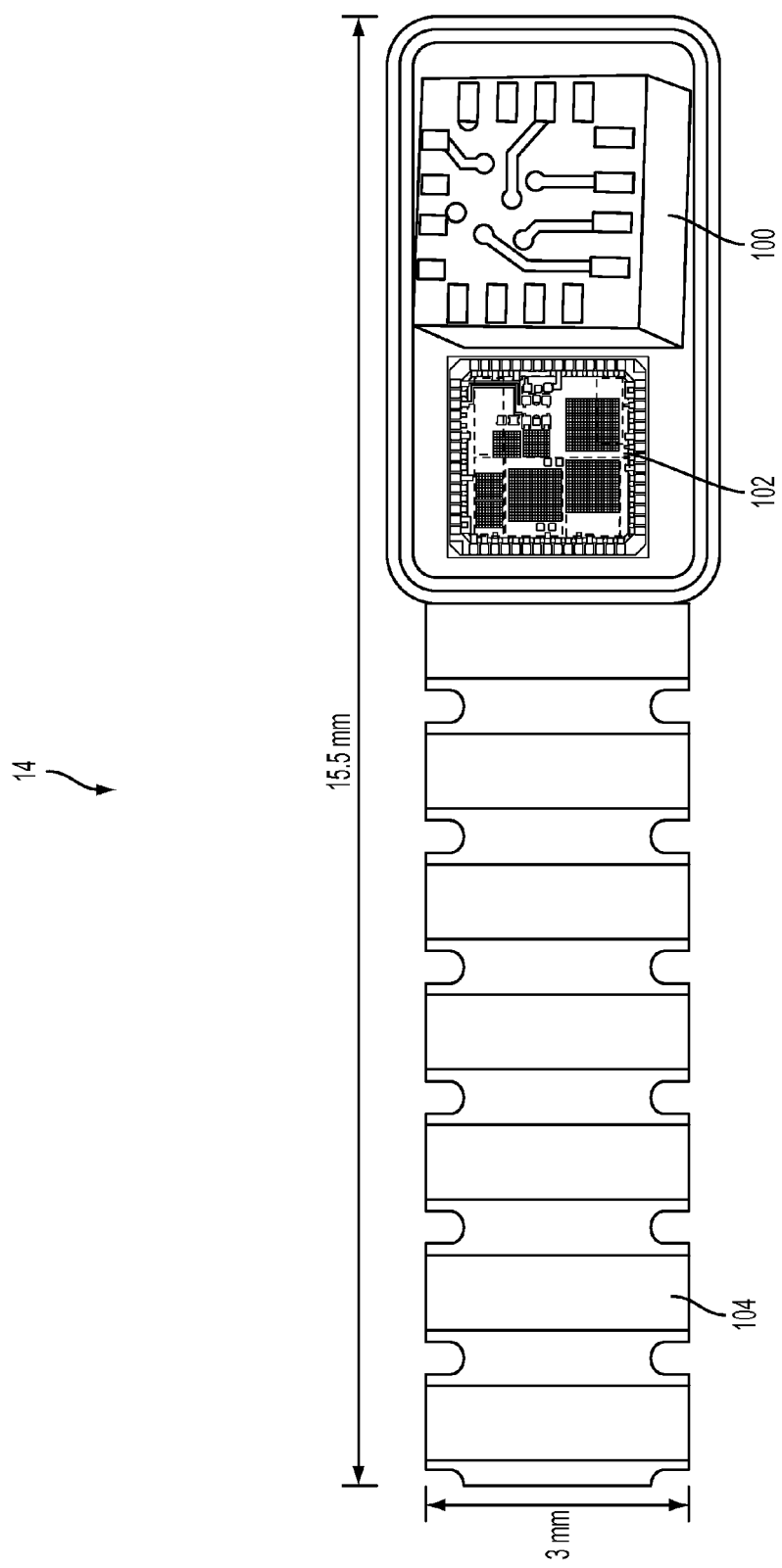
FIG. 9 illustrates at least one embodiment of an active transponder that may be used with the wireless magnetic tracking system of FIG. 1 and/or the wireless magnetic tracking system of FIG. 8.

One illustrative embodiment of an active transponder 14, which may be used with the wireless magnetic tracking system 10 and/or the wireless magnetic tracking system 80, is shown in FIG. 9. As indicated in FIG. 9, this illustrative embodiment of the transponder 14 has dimensions of 3 millimeters by 15.5 millimeters, making the transponder 14 suitable to be implanted in the tissue of a patient 22 undergoing radiation therapy. The transponder 14 generally includes a plurality of magneto-resistive sensors 100 (which has dimensions of about 3 by 3 millimeters), an integrated circuit chip 102 (which has dimensions of about 2 by 2 millimeters), and an antenna 104.

Figure 10:
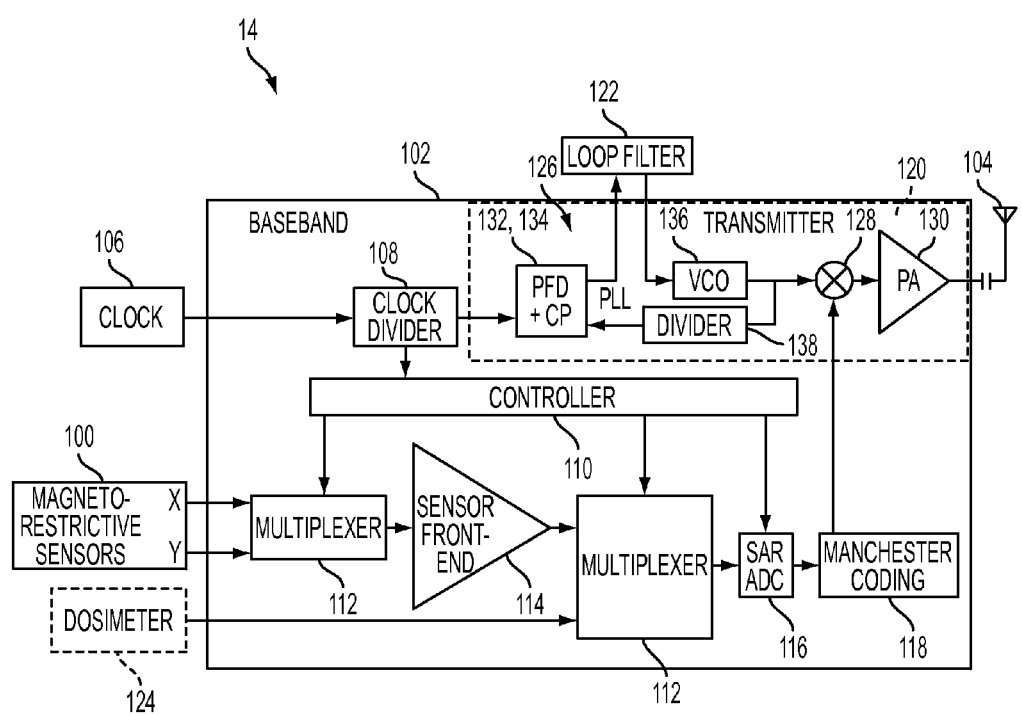
FIG. 10 is a simplified diagram of a number of components of the active transponder of FIG. 9.

Various components of the transponder 14, including the components implemented on the integrated circuit chip 102, are illustrated as a simplified block diagram in FIG. 10. In the illustrative embodiment of FIG. 10, the transponder 14 includes a plurality of magneto-resistive sensors 100, an antenna 104, a clock 106, a clock divider 108, a controller 110, a number of multiplexers 112, a sensor front-end circuit 114, an analog-to-digital converter ("ADC") 116, a Manchester coding circuit 118, a transmitter 120, a loop filter 122, and a power supply (not shown). In some embodiments, the transponder 14 may also optionally include a dosimeter 124 configured to measure an amount of radiation delivered to the transponder 14. In the illustrative embodiment, the transmitter 120 of transponder 14 includes an integer-N phase-locked loop ("PLL") 126, a modulator 128, and a power amplifier 130. The integer-N PLL 126, in turn, includes a phase frequency detector 132, a charge pump 134, a voltage-controlled oscillator ("VCO") 136, and a frequency divider 138.

Figure 11:
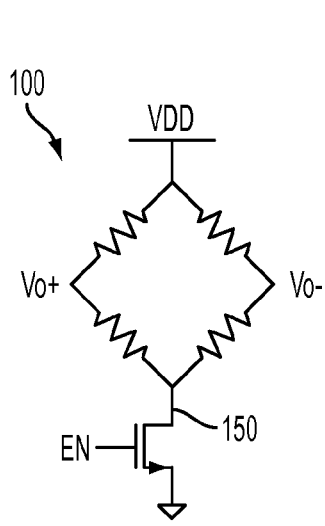
FIG. 11 is a simplified circuit diagram of at least one embodiment of a magneto-resistive sensor of the active transponder of FIGS. 9 and 10.

Referring now to FIG. 11, a simplified circuit diagram of an illustrative magneto-resistive sensor 100 is shown. This illustrative magneto-resistive sensor 100 utilizes a wheatstone bridge topology to reduce the effect of temperature drift. The current consumption of a wheatstone bridge is directly proportional to the supply voltage (VDD). To reduce the power consumption of the transponder 14, 0.5 V was chosen as a supply voltage for the sensor 100. At 0.5 V, the power consumption of the illustrative magneto-resistive sensor 100 is about 250 µW. Thus, the power consumption of a bi-axial sensor 100 is about 500 µW. A supply voltage of 0.5 V has been utilized for the entire transponder 14 to avoid the unnecessary complexity of multiple supply voltages. The magneto-resistive sensor 100 also includes an enable switch (EN) 150 to further reduce power consumption when the bridge is not in use. The enable switch 150 is configured to selectively connect (and disconnect) the magneto-resistive sensor 100 to the supply voltage. When disconnected from the supply voltage, the magneto-resistive sensor 100 consumes no power.

As noted above, the transponder 14 includes a plurality of magneto-resistive sensors 100, each of which is configured to measure a different component of a magnetic field. In some embodiments, the transponder 14 may include three magneto-resistive sensors, each of which is configured to measure components of the magnetic field that are normal to one another (i.e., a tri-axial magnet sensor 100). These magneto-resistive sensors 100 each output an analog voltage signal in response to a magnetic field. Each of the magneto-resistive sensors 100 included in the transponder 14 may have the design shown in FIG. 11 and described above. In some embodiments, the controller 110 may be configured to sequentially activate the enable switches 150 on each of the plurality of magneto-resistive sensors 100, so that a particular sensor 100 consumes power only when needed to measure a magnetic field.

Figure 12A:
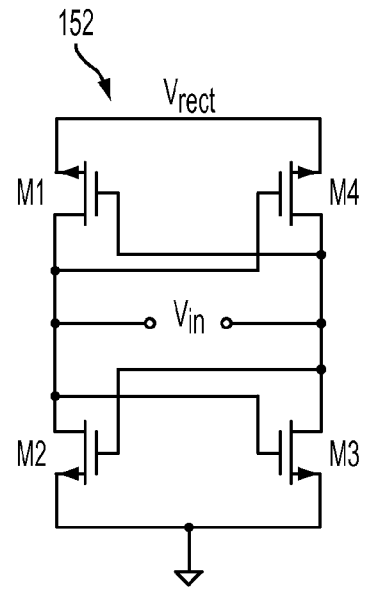
FIG. 12A is a simplified circuit diagram of at least one embodiment of a rectifier of a power supply of the active transponder of FIGS. 9 and 10.
Figure 12B:
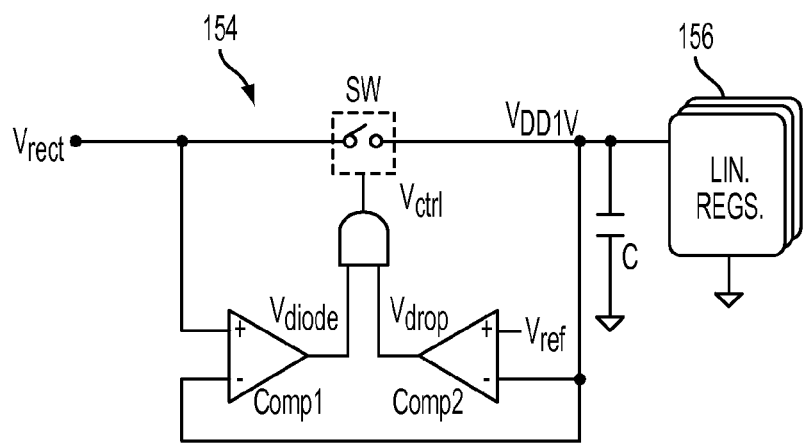
FIG. 12B is a simplified circuit diagram of at least one embodiment of a voltage regulator of the power supply of the active transponder of FIGS. 9 and 10.

In some embodiments, the transponder 14 may include a power supply configured to wirelessly receive energy at a frequency between 1 MHz and 10 MHz. Electromagnetic energy in this frequency range penetrates the human body with minimal loss. One illustrative embodiment of a wireless power supply that may be included in the transponder 14 is shown in FIGS. 12A and 12B. Electromagnetic energy is received and rectified by the rectifier 152 shown in FIG. 12A ($V_{in}$ being the input to the rectifier 152 and $V_{rect}$ being the output of the rectifier 152). The voltage regulator 154, shown in FIG. 12B, then regulates and filters $V_{rect}$ to provide a 0.5 V supply voltage to the components of the transponder 14. The linear regulators 156 of the voltage regulator 154 produce a power output with a power efficiency of 15%, a ripple on the 1 V node of 0.2 Vpp, a ripple on the 0.5 V node of about 30 mV, and an output power of 1.2 mW. It is also contemplated that the transponder 14 may be powered from other sources, such as a battery.

Figure 13:
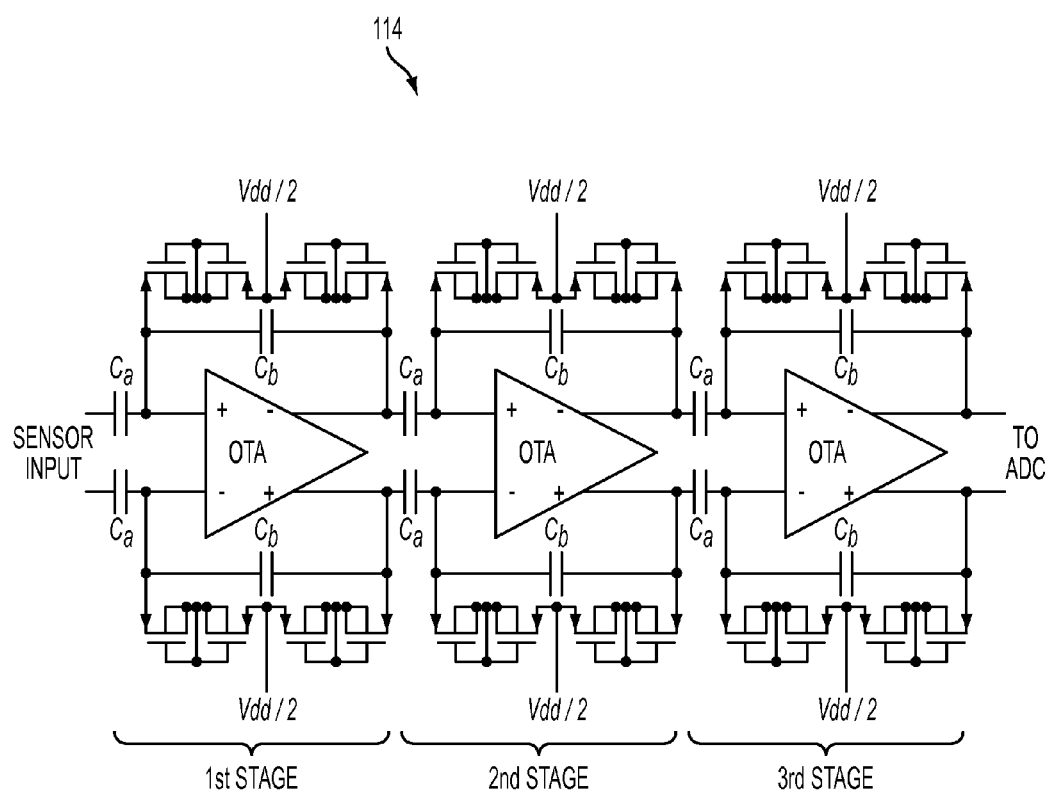
FIG. 13 is a simplified circuit diagram of at least one embodiment of a sensor front-end circuit of the active transponder of FIGS. 9 and 10.

The sensor front-end circuit 114 of the illustrative embodiment of transponder 14 is shown in FIG. 13. The sensor front-end circuit 114 may provide amplification and/or band-pass filtering to an analog voltage signal output by one of the plurality of magneto-resistive sensors 100 (and passed by the multiplexer 112 to the sensor front-end circuit 114). As shown in FIG. 13, the sensor front-end circuit 114 comprises three stages of amplification. The mid-band gain of each stage is determined by the capacitor ratio, $C_a/C_b$, of that stage. In the illustrative embodiment, the mid-band gain of each stage is 20 dB, making an overall mid-band gain of the sensor front-end circuit 114 around 60 dB. Additionally, the illustrative sensor front-end circuit 114 has a low cut-off frequency of about 10 Hz and a high cut-off frequency of about 20 kHz, which provides band-pass filtering. In the illustrative embodiment, the overall power consumption of the sensor front-end circuit is about 79 μW.

Figure 14:
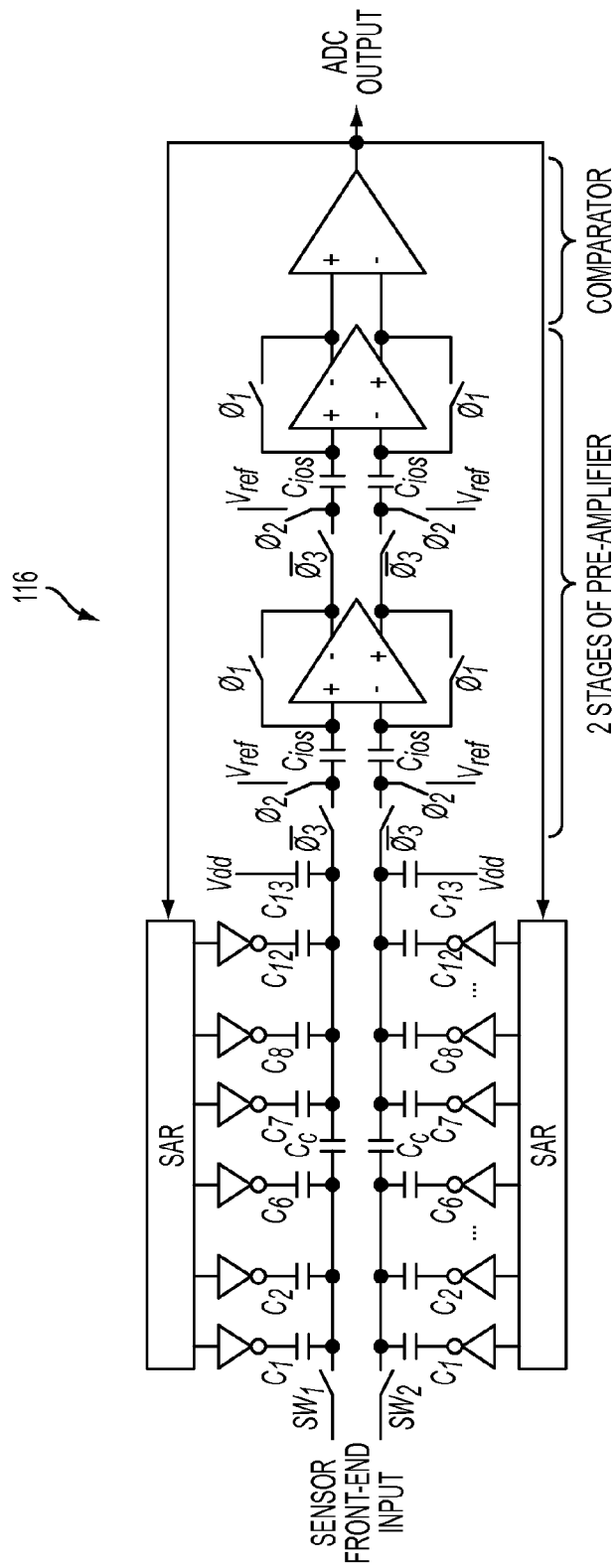
FIG. 14 is a simplified circuit diagram of at least one embodiment of an analog-to-digital converter ("ADC") of the active transponder of FIGS. 9 and 10.

The output of the sensor front-end circuit 114 (or an output of the dosimeter 124) is passed by a multiplexer 112 to the ADC 116. The ADC 116 is configured to convert a received analog voltage signal into a digital signal for presentation to the transmitter 120. FIG. 14 shows a simplified circuit diagram of one illustrative embodiment of an ADC 116 that may be utilized in the transponder 14. As shown in FIG. 14, the ADC 116 is embodied a successive approximation register ("SAR") ADC 116. In the illustrative embodiment, the inputs (SWI, SW2) to the SAR ADC 116 are bootstrapped switches that allow rail-to-rail inputs. The capacitors $C_1$-$C_{13}$ and $C_c$ form a split capacitor array that acts as a digital-to-analog converter ("DAC"). Due to the supply voltage of 0.5 V, the SAR ADC 116 utilizes inverters instead of switches to charge and discharge the capacitors in the array. Monotonic switching is also utilized in the SAR ADC 116 to keep the charging and discharging of capacitors to a minimum, which further reduces power consumption. The illustrative embodiment uses two stages of pre-amplifiers to prevent kickback effect from the comparator, as well as to reduce the offset of the comparator. The SAR ADC 116 of the illustrative embodiment has a power consumption of about 12 μW.

The transmitter 120 of the transponder 14 is configured to generate an output signal by modulating a carrier signal with the digital signal output by the ADC 116. The transmitter 120 comprises an integer-N PLL 126 that generates the carrier signal. A modulator 128 of the transmitter 120 overlays the digital signal output by the ADC 116 on top of this carrier signal to create the output signal. Before broadcasting the output signal on the antenna 104, the transmitter 120 amplifies the output signal using a power amplifier 130. In the illustrative embodiment, the power amplifier is embodied as a non-linear, inverter-based power amplifier that produces about −12 dBm output power and consumes about 235 μW of power.

Figure 15:
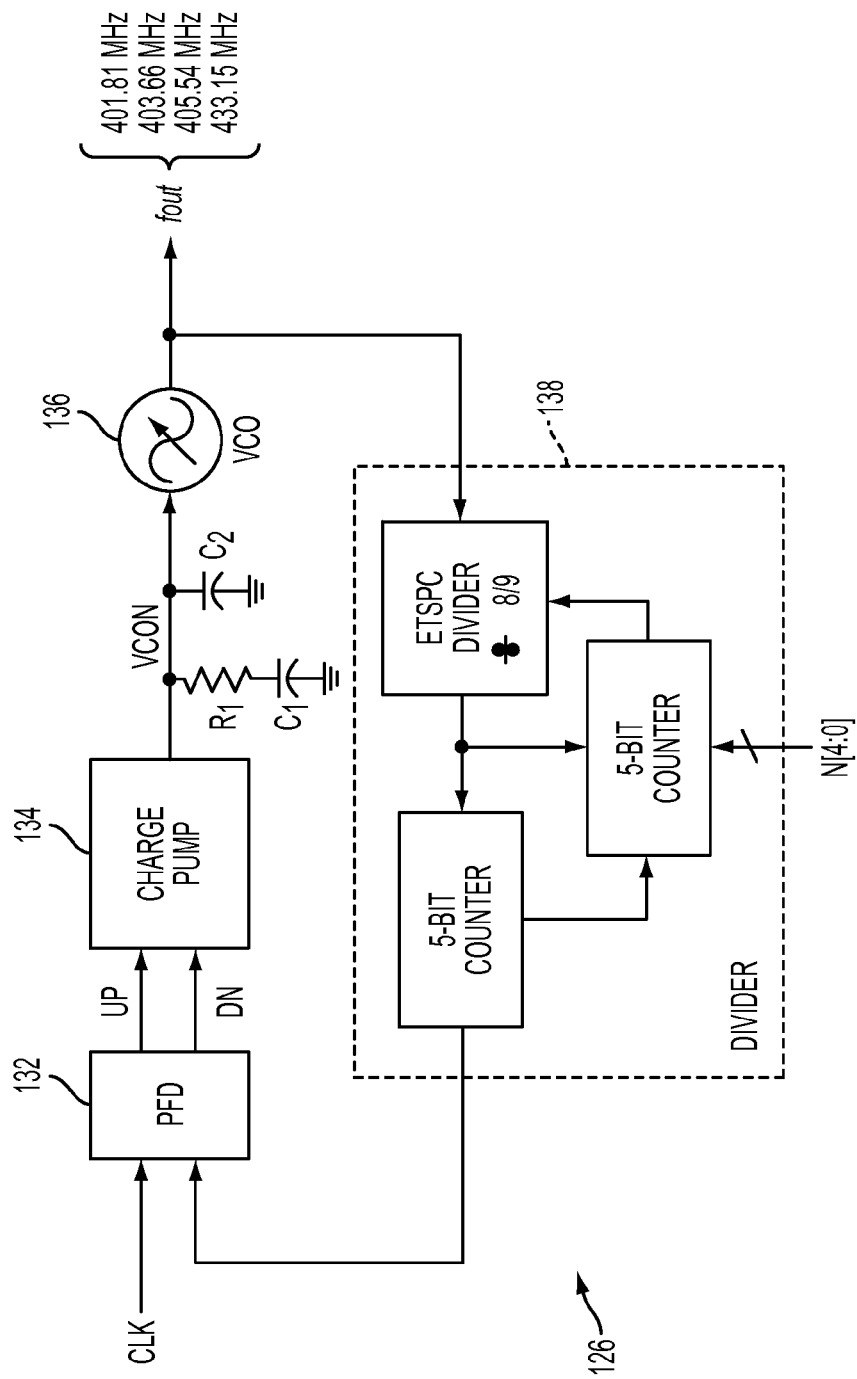
FIG. 15 is a simplified circuit diagram of at least one embodiment of an integer-N phase-locked loop ("PLL") of the active transponder of FIGS. 9 and 10.
Figure 16:
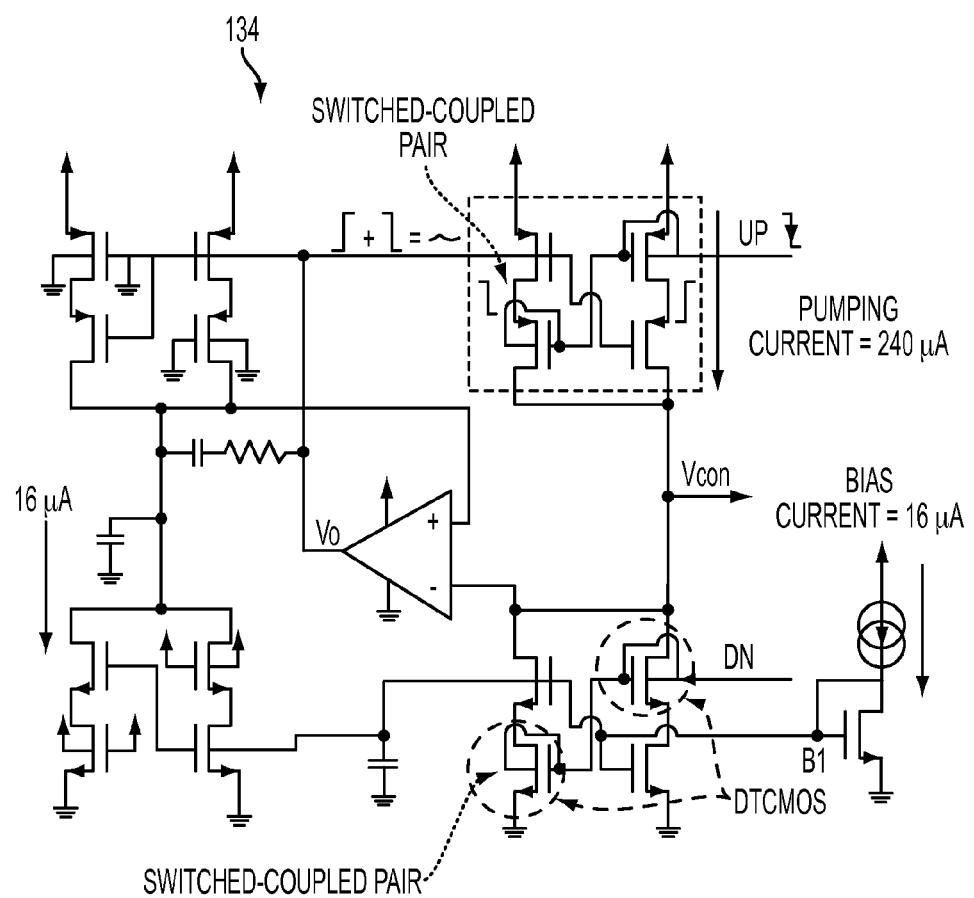
FIG. 16 is a simplified circuit diagram of at least one embodiment of a charge pump of the integer-N PLL of FIG. 15.

One illustrative embodiment of an integer-N PLL 126 that may be used in the transmitter 120 is shown in FIG. 15. The PLL 126 of FIG. 15 is configured to generate three frequencies (401.81 MHz, 403.66 MHz and 405.54 MHz) that fall within the MedRadio band and one frequency (433.15 MHz) that falls within the ISM band. The PLL 126 includes a phase frequency detector 132, a charge pump 134 with low static power but high current output, a low-power ring-based VCO 136, and a pulse-swallow counter with a dual-modulus prescaler 138. To utilize a 0.5 V supply voltage, a resistor-varactor tuning method is utilized in the VCO 136. The resistor tuning provides coarse frequency tuning, while the varactor tuning provides fine frequency tuning Additionally, the charge pump 134 (one illustrative embodiment of which is shown in FIG. 16) may use dynamic threshold transistors ("DTCMOS") to reduce the leakage current. In a dynamic threshold transistor, a body and a gate of the transistor are electrically coupled to one another, so that the threshold voltage of the transistor changes based on the gate signal. The illustrative embodiment of the integer-N PLL 126 shown in FIG. 15 has a loop bandwidth of about 150 kHz, a reference spur of about −38.2 dBc, phase noise at 1 MHz offset of about −91.5 dBc/Hz, and an overall power consumption of about 440 μW.

Figure 17:
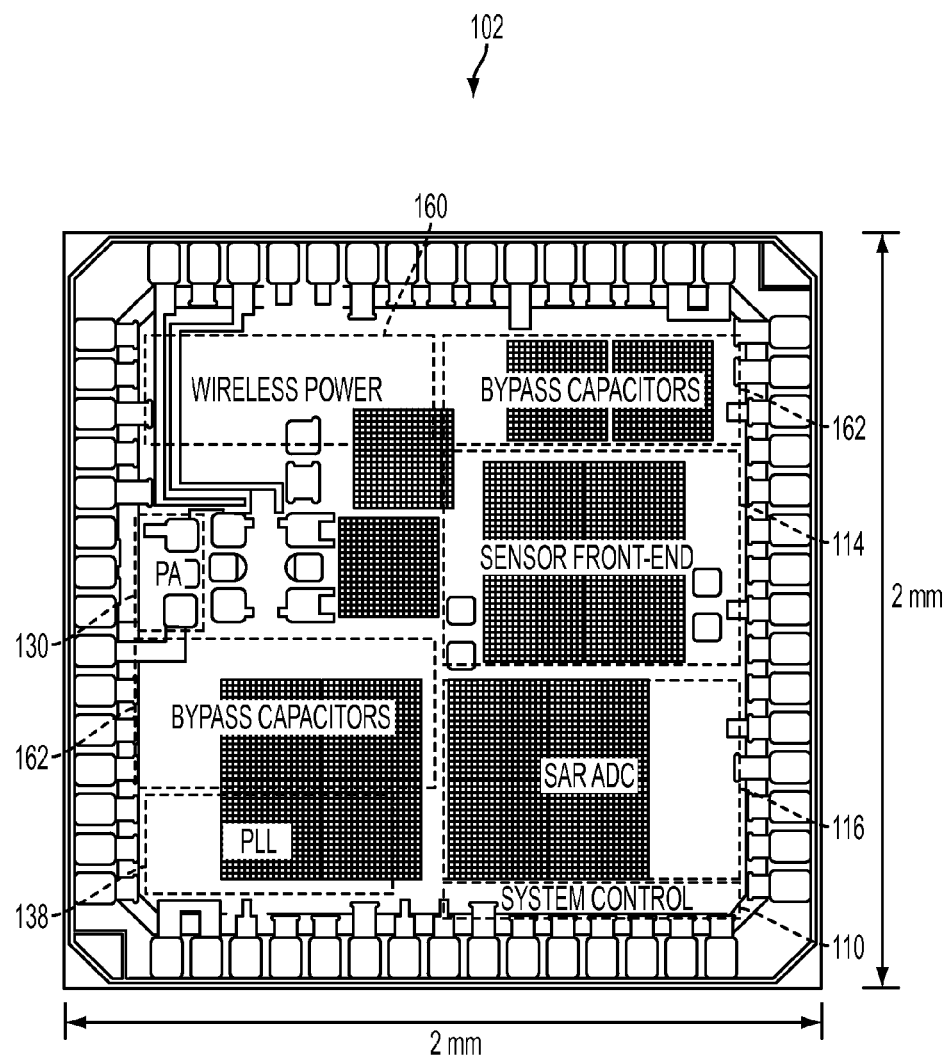
FIG. 17 illustrates a number of components of the active transponder of FIGS. 9 and 10 implemented on an integrated circuit chip.

Referring now to FIG. 17, a number of components of the active transponder 14 were implemented on an integrated circuit chip 102, including the transmitter 120 (PLL 126 shown in FIG. 17), the SAR ADC 116, the controller 110, the sensor front-end circuit 114, power amplifier 130, and the wireless power supply 160, as well as bypass capacitors 162 of the transponder 14. As illustrated in FIG. 17, the foregoing components have a combined chip area of less than four square millimeters. The illustrative embodiment of FIG. 17 was implemented in 130-nm CMOS technology. The active transponder described herein achieves a total power consumption that is less than 1 mW.

Figure 18:
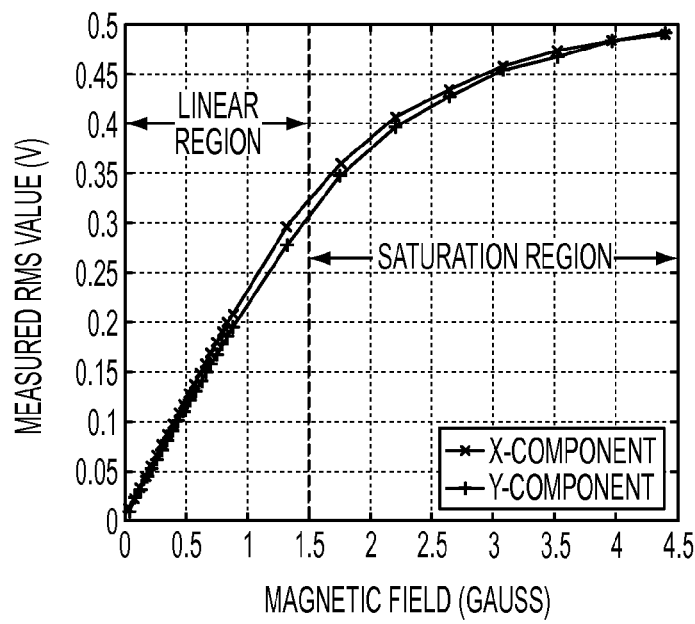
FIG. 18 illustrates a relationship between an analog voltage signal supplied to the ADC of FIG. 14 and the magnetic field.

FIG. 18 illustrates a plot of RMS value of an analog voltage signal supplied to the ADC 116 for different sinusoidal magnetic field strengths (B). The plot is divided into two regions: a "linear" region for B<1.5 gauss and "saturation" region for B>1.5 gauss. In the linear region, the measured RMS value is linearly related (i.e., generally directly proportional) to B. In the saturation region, however, the measured RMS value starts to approach a constant value because the sensor front-end circuit 114 starts to saturate. As the magnetic field used in the present wireless magnetic tracking system 10 is less than 1.5 gauss, the sensing region of the transponder 14 falls into the linear region shown on FIG. 18.

Figure 19:
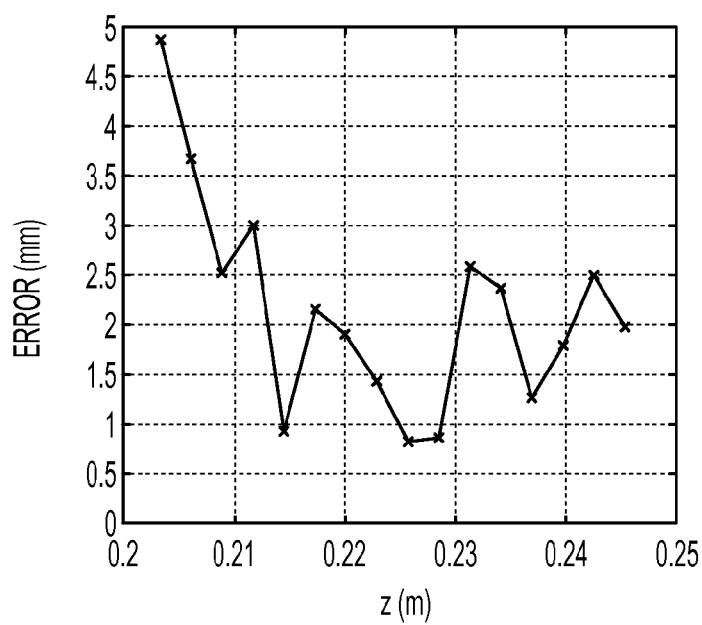
FIG. 19 is a graph of experimental error for at least one embodiment of a wireless magnetic tracking system.

The real-time tracking accuracy of the wireless magnetic tracking system 10 was experimentally tested. The results of this experimental testing are shown in the plot of FIG. 19. A transponder 14 was placed in the middle of four transmitting coils 12 and controlled by micropositioners. As reflected in FIG. 19, the presently disclosed wireless magnetic tracking system 10 is able to determine the position and the orientation of the active transponder 14 relative to the transmitting coils 12 with an error of less than 5 millimeters.

While certain illustrative embodiments have been described in detail in the drawings and the foregoing description, such an illustration and description is to be considered as exemplary and not resistive in character, it being understood that only illustrative embodiments have been shown and described and that all changes and modifications that come within the spirit of the disclosure are desired to be protected. There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of systems and methods that incorporate one or more of the features of the present invention and fall within the spirit and scope of the present disclosure.

The invention claimed is:

1. A wireless magnetic tracking system comprising: a plurality of transmitting coils each configured to generate a magnetic field when energized;
   an active transponder configured to simultaneously (i) obtain measurements of the magnetic field when one of the plurality of transmitting coils is energized and (ii) transmit a wireless signal containing data concerning the measurements;
   a computing device configured to (i) cause each of the plurality of transmitting coils to be sequentially energized, (ii) receive the data concerning the measurements, and (iii) determine a position and an orientation of the active transponder relative to the plurality of transmitting coils in response to the data concerning the measurements;
   a coil driver circuit configured to selectively supply an excitation signal to each of the plurality of transmitting coils, wherein the computing device is configured to control the coil driver circuit; and a receiver configured to (i) receive the wireless signal from the active transponder and (ii) provide the data concerning the measurements to the computing device;

wherein the receiver comprises a plurality of antennas configured to simultaneously receive the wireless signal from the active transponder and a combiner configured to sum the wireless signals received by the plurality of antennas.

2. The wireless magnetic tracking system of claim 1, wherein the active transponder is adapted to be implantable in a patient's tissue.

3. The wireless magnetic tracking system of claim 1, wherein the active transponder comprises at least two magneto-resistive sensors, each of the at least two magneto-resistive sensors being configured to measure a different component of the magnetic field.

4. The wireless magnetic tracking system of claim 3, wherein the at least two magneto-resistive sensors comprise three magneto-resistive sensors, the three magneto-resistive sensors being configured to measure components of the magnetic field that are normal to one another.

5. The wireless magnetic tracking system of claim 1, wherein the computing device is configured to control the coil driver circuit such that each of the plurality of transmitting coils is energized over an integer multiple of a period of the excitation signal.

6. The wireless magnetic tracking system of claim 1, wherein the computing device is configured to control the coil driver circuit such that each of the plurality of transmitting coils is grounded when not being energized.

7. The wireless magnetic tracking system of claim 1, wherein the excitation signal is a pulsed direct-current excitation signal.

8. The wireless magnetic tracking system of claim 1, further comprising a receiver configured to (i) receive the wireless signal from the active transponder and (ii) provide the data concerning the measurements to the computing device.

9. The wireless magnetic tracking system of claim 1, wherein the receiver is configured to integrate a multiplication product of the wireless signal received from the active transponder and the excitation signal supplied by the coil driver circuit.

10. The wireless magnetic tracking system of claim 1, further comprising an additional active transponder, the additional active transponder being configured to simultaneously (i) obtain additional measurements of the magnetic field when one of the plurality of transmitting coils is energized and (ii) transmit an additional wireless signal containing data concerning the additional measurements, wherein the wireless signal and the additional wireless signal have different carrier radio frequencies.

11. The wireless magnetic tracking system of claim 1, wherein the computing device is configured to determine the position and the orientation of the active transponder relative to the plurality of transmitting coils in six degrees of freedom.

12. The wireless magnetic tracking system of claim 1, wherein the computing device is configured to determine the position and the orientation of the active transponder relative to the plurality of transmitting coils using an iterative method with a previously determined position and orientation of the active transponder as an initial guess.

13. The wireless magnetic tracking system of claim 1, wherein the computing device is further configured to re-determine the position and the orientation of the active transponder relative to the plurality of transmitting coils each time another one of the plurality of transmitting coils is energized.

14. The wireless magnetic tracking system of claim 1, wherein the computing device is configured to determine the position and the orientation of the active transponder relative to the plurality of transmitting coils with an error of less than 5 millimeters.

15. The wireless magnetic tracking system of claim 1, wherein the plurality of transmitting coils consists of two transmitting coils.

* * * * *